US007067505B2

(12) United States Patent
King et al.

(10) Patent No.: US 7,067,505 B2
(45) Date of Patent: Jun. 27, 2006

(54) DI-STEROIDAL PRODRUGS OF ESTRADIOL

(75) Inventors: John Alexander King, Sallins (IE); James Keown, Kilkeel (IE); James William McIlroy, Belfast (IE); William Paul Armstrong, Belfast (IE); Michael Anthony McKervey, Belfast (IE); Austin McMordie, Craigavon (IE)

(73) Assignee: Warner Chilcott Company, Inc., Fajardo, PR (US)

( * ) Notice: Subject to any disclaimer, the term of this patent is extended or adjusted under 35 U.S.C. 154(b) by 0 days.

(21) Appl. No.: 11/009,618

(22) Filed: Dec. 10, 2004

(65) Prior Publication Data
US 2005/0159399 A1 Jul. 21, 2005

Related U.S. Application Data

(60) Provisional application No. 60/536,527, filed on Jan. 15, 2004.

(51) Int. Cl.
C07N 31/56 (2006.01)
C07J 9/00 (2006.01)
C07C 49/00 (2006.01)
C07C 49/423 (2006.01)

(52) U.S. Cl. ............ 514/182; 514/169; 514/170; 552/201; 552/203; 552/205; 552/502; 552/540; 552/541

(58) Field of Classification Search .......... 552/541, 552/540, 201, 203, 205; 514/169, 182, 177
See application file for complete search history.

(56) References Cited

U.S. PATENT DOCUMENTS

| | | | | |
|---|---|---|---|---|
| 3,766,223 A * | 10/1973 | Ercoli et al. | ......... | 552/509 |
| 3,828,081 A | 8/1974 | Ercoli et al. | ......... | 260/397.2 |
| 3,916,002 A | 10/1975 | Taubert et al. | ......... | 260/397.4 |
| 3,952,030 A | 4/1976 | Chambers et al. | ......... | 260/397.4 |
| 4,002,747 A | 1/1977 | van der Vies | ......... | 424/243 |
| 4,198,405 A | 4/1980 | Enomoto et al. | ......... | 424/242 |
| 4,310,511 A | 1/1982 | Holick | ......... | 424/59 |
| 5,117,015 A | 5/1992 | Yarino et al. | ......... | 552/541 |
| 5,610,149 A | 3/1997 | Burrows et al. | ......... | 514/169 |
| 5,888,996 A | 3/1999 | Farb | ......... | 514/182 |
| 5,955,068 A | 9/1999 | Gouin et al. | ......... | 424/78.17 |
| 5,989,581 A | 11/1999 | Groenewegen | ......... | 424/433 |
| 6,083,941 A | 7/2000 | Farb | ......... | 514/177 |
| 6,375,930 B1 | 4/2002 | Young et al. | ......... | 424/9.362 |
| 6,441,206 B1 | 8/2002 | Mikkonen et al. | ......... | 552/540 |
| 2002/0131991 A1 | 9/2002 | Milstein et al. | ......... | 424/439 |

FOREIGN PATENT DOCUMENTS

| | | |
|---|---|---|
| DE | 1 123 666 | 10/1959 |
| DE | 2 330 581 | 1/1975 |
| FR | 2 297 629 | 1/1975 |
| JP | 35-004967 | 5/1960 |
| NL | 7 308 083 | 12/1974 |
| WO | WO 98/52965 | 11/1998 |

OTHER PUBLICATIONS

K. Parfitt, "Martindale—The Complete Drug Reference," 32ed, 1999, Pharmaceutical Press, pp. 1455-1458.
K. Fotherby, "Intrasubject Variabiity in the Pharmacokinetics of Ethynyloestradiol," Journal of Steroid Biochemistry and Molecular Biology, vol. 38, No. 6, 1991, pp. 733-736.
K. Fotherby, "Pharmacokinetics of Ethynyloestradiol in Humans," Methods and Findings in Experimental Clinical Pharmacology, 1982, 4(2), pp. 133-141.
E. Diczfalusy, O. Ferno, H. Fex, and B. Hogberg, "Long-Acting p-Alkoxyhydrocinnamic Acid Esters of Steroid Hormones," Acta Chemica Scandinavica, 1963, 17, pp. 2536-2547.
J. Fried and N.A. Abraham, "The Effect of Co-Solvents on Metal in Ammonia Reductions, The Formations of Dimeric Steroid Hormones," Tetrahedron Letters, 1964, No. 28, pp. 1879-1885.
H. Kuhl and H. Taubert, "A New Class of Long-Acting Hormonal Steroid Preparation: Synthesis of Oligomeric Estradiol Derivatives," Steroids, Jul. 1973, 22, pp. 73-87.
H. Kuhl and H. Taubert, "A New Class of Long-Acting Hormonal Steroid Prepartion: Synthesis of Dimeric Ethynodiol and Nortestosterone, or Dimeric and Trimeric Androgens and of Some Dimeric Combinations of Steroids," Steroids, 1974, vol. 24, No. 5, pp. 613-626.
H. Kuhl, W. Auerhammer, and H. Taubert, "Oligomeric Oestradiol Esters: A New Class of Long-Acting Oestrogens," Acta Endrocinologica, 1976, 83, pp. 439-448.
R. Vitali, S. Gladiali, G. Falconi, G. Celasco, M.A. Saccani, and R. Gardi, "Disteroidyl Ethers. 1. Synthesis and Oral Long-Lasting Uterotrophic Activity of 1,3,5(10)-Estratrien-17-yl Enol Ethers of 3-Keto Steroids," Journal of Medicinal Chemistry, 1977, vol. 20, No. 3, pp. 359-364.
A. Ius, G. Meroni, and L. Ferrara, "Two Dimers, 4:4' and 2:2'-Di[estradiol], Obtained by Chemical Oxidative Coupling of Estradiol," Journal of Steroid Biochemistry, vol. 8, pp. 1259-1261.

(Continued)

Primary Examiner—Sabiha Qazi
(74) Attorney, Agent, or Firm—Fitzpatrick, Cella, Harper & Scinto

(57) ABSTRACT

The present invention is a di-steroidal prodrug of estradiol having the following formula:

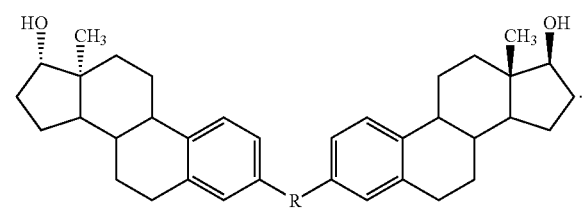

14 Claims, No Drawings

OTHER PUBLICATIONS

D. Rabbouin, V. Perron, B. N'Zemba, R. Gaudreault, and G. Berube, "A Facile Synthesis of $C_2$- Symmetric 17β-Estradiol Di3mers," Bioorganic & Medicinal Chemistry Letters, 2003, 13, pp. 557-560.

Hu Zheng et al., Abstract of "Studies on polymer-supported drugs: synthesis of poly(ethylene glycol)-estrogen compounds," Chemical Abstracts Service (XP002322263), and Yaoxue Xuebao (Database Accession No. 1988:423178), 1987, 22(8), 637-40.

Huai-De Shu et al., Abstract of "Structure-activity relationships of estradiol derivatives," Chemical Abstracts of Service (XP002322264), and Yaoxue Xuebao (Database Accession No. 1979:604845), 1979, 14(6), 343-8.

W. Dirscherl, "Uber Kohlensaurederivate des Follikelhormons. 7. Mittellung uber Sexualhormone und verwandte Stoffe" Hoppe Seyler Zeitschrift Fur Physiol. Chemie, vol. 239, 1936, pp. 49-52. Translation included.

* cited by examiner

DI-STEROIDAL PRODRUGS OF ESTRADIOL

CROSS REFERENCE TO RELATED APPLICATIONS

This application claims the benefit of U.S. Provisional Patent Application No. 60/536,527, filed on Jan. 15, 2004.

BACKGROUND OF THE INVENTION

1. Field of the Invention

This invention is directed to a di-steroidal prodrug of estradiol and pharmaceutically acceptable salts thereof. The invention also includes pharmaceutical dosage units of the di-steroidal prodrug and a method of forming the di-steroidal prodrug of estradiol.

2. Related Background Art

Unbound 17β-estradiol is the most active, naturally occurring human estrogen. However, due to poor absorption and extensive first-pass metabolism in the gastrointestinal tract and liver following oral absorption, it is not generally orally active. Several methods have been utilized to increase its oral activity. A micronized form (to provide an increased surface area of drug for absorption) of estradiol which has sufficient oral bioavailability to be active is available. Alternatively estradiol can be formulated as a conjugate, e.g., conjugated equine estrogens which are essentially estrogen metabolites purified from the urine of pregnant mares that contain sulphate and glucuronide derivatives (Martindale 32$^{ed}$, 1999, Pharmaceutical Press). These conjugates are orally active as they are hydrolyzed by enzymes in the lower gastrointestinal tract allowing absorption of the active estrogen. Another alternative is the oral administration of estradiol esters. Such compounds are known in the art for oral administration of estrogen and include estradiol-3,17-diacetate, estradiol-17-acetate, estradiol-3,17-valerate, estradiol-3-valerate and estradiol-17-valerate. These esters rapidly hydrolyze to free estradiol following oral administration.

U.S. Pat. No. 3,916,002 to Taubert et al. describes a number of oligomeric esters of androgenic, estrogenic and progestogenic steroids having the formula: R—O—CO—(CH$_2$)$_n$—CO—O—R, wherein n is between 2 and 8, and each R is a monovalent steroid radical. The steroid radical is derived from steroids having a hydroxyl substituent at one of the carbon atoms numbered 3, 16 or 17. They can be produced by esterification of the two carboxyl radicals of a dicarboxylic acid with a steroid alcohol having a hydroxyl radical substituent at carbon atoms numbered 3, 16, or 17. However, Taubert et al. does not disclose a novel di-steroidal prodrug of estradiol that is linked at the 3' C position of the estradiol moiety.

A novel prodrug of estradiol that may increase oral activity would be highly advantageous.

SUMMARY OF THE INVENTION

The present invention is a di-steroidal prodrug of estradiol according to formula I:

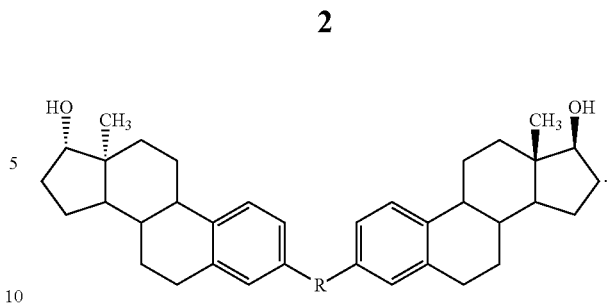

and pharmaceutically acceptable salts thereof; wherein R is selected from the group consisting of

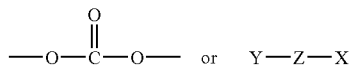

wherein X and Y are independently selected from

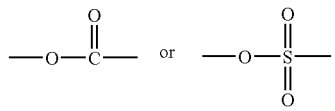

and Z is (i) an aliphatic straight chain having 1 to 10 carbon atoms which may be saturated or unsaturated and optionally may be substituted by one or more lower alkyl, hydroxy or amino groups, (ii) A-B-D wherein A and D are independently

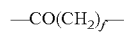

wherein f is 0 to 5, and B is —O—(CH$_2$CH$_2$O)$_p$—, wherein p is 1 to 700, or (iii) a peptide linkage having 2 to 15 amino acid units derived independently from amino acids selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or combinations thereof wherein the end groups of the peptide are amino acid units independently derived from aspartic acid and glutamic acid.

The present invention also includes a pharmaceutical dosage unit comprising (a) a di-steroidal prodrug of estradiol according to formula I, and (b) one or more pharmaceutically acceptable excipients. In a particularly preferred embodiment, a progestogen is included in the pharmaceutical dosage unit.

The present invention also includes a method for forming a di-steroidal prodrug of estradiol having the structure of formula I, comprising the step of reacting estradiol and a linking agent under conditions effective to form the di-steroidal prodrug of estradiol. Optionally, the process may include further purification steps such as chromatography or recrystallization.

In another aspect of the present invention, a method of providing contraception is provided. The method comprises the step of administering to a patient in need thereof, an effective amount of a di-steroidal prodrug of estradiol of the invention, for an effective period of time.

In yet another aspect of the invention, a method of providing hormone treatment therapy is provided. The method comprises the step of administering to a patient in need thereof, an effective amount of a di-steroidal prodrug of estradiol of the invention, for an effective period of time.

DETAILED DESCRIPTION OF THE INVENTION

For the purposes of the present invention, a prodrug is an entity which either comprises an inactive form of an active drug or includes a chemical group which confers preferred characteristics on the drug.

For the purposes of the present invention, room temperature is understood to mean 25° C.+/−5° C.

In the present invention, the di-steroidal prodrugs of estradiol have estradiol moieties that are linked by a divalent linking group R at the 3' C position of the estradiol moiety. The linking group R is preferably selected from the group consisting of a carbonate group or a dicarboxylic group having an aliphatic backbone of 2 to 10 carbon atoms which may be saturated or unsaturated, straight or branched, and which optionally may be substituted by amino, hydroxyl or lower alkyl. As used herein lower alkyl is a straight chain or branched aliphatic group having 1 to 6 carbon atoms. In another embodiment R may be a dicarboxylic group having a polyoxyethylene backbone. In yet a further embodiment the linking group may be a peptide with a carboxylic acid function at each end.

In the present invention the di-steroidal prodrug of estradiol of the invention has the structural formula: Formula:

Formula 1

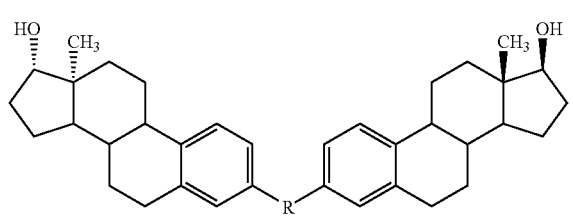

wherein R is selected from the group consisting of

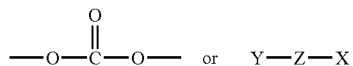

wherein X and Y are independently selected from

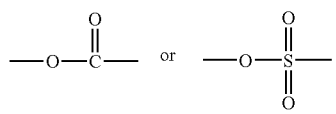

and Z is
(i) an aliphatic straight chain having 1 to 10 carbon atoms which may be saturated or unsaturated and optionally may be substituted by one or more lower alkyl, hydroxy or amino groups, (ii) A-B-D wherein A and D are independently

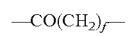

wherein f is 0 to 5, and B is —O—$(CH_2CH_2O)_p$—, wherein p is 1 to 700, or (iii) a peptide linkage having 2 to 15 amino acid units derived independently from amino acids selected from the group consisting of alanine, arginine, asparagine, aspartic acid, cysteine, glutamine, glutarnic acid, glycine, histidine, isoleucine, leucine, lysine, methionine, phenylalanine, proline, serine, threonine, tryptophan, tyrosine, valine, or combinations thereof wherein the end groups of the peptide are amino acid units independently derived from aspartic acid and glutamic acid.

It should be apparent that when Y and X are a carboxylic or sulfonic group that the carbonyl or sulfur of those groups is bound to Z. Thus, in a preferred embodiment when Y and X are both carbonyl then R is

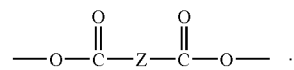

It should be further apparent to one of ordinary skill in the art that the stereochemical conformation of each estradiol moiety in the di-steroidal prodrug will be dependent on the structural conformation of R.

In a preferred embodiment, R is selected from the group consisting of:

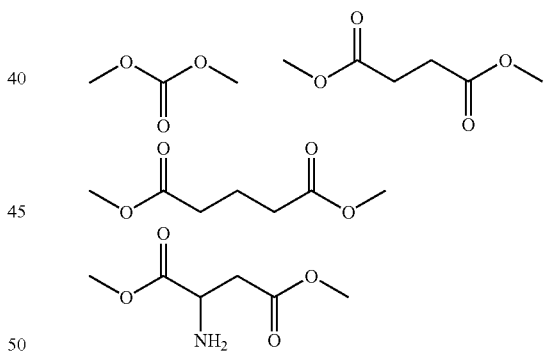

In another embodiment, R is

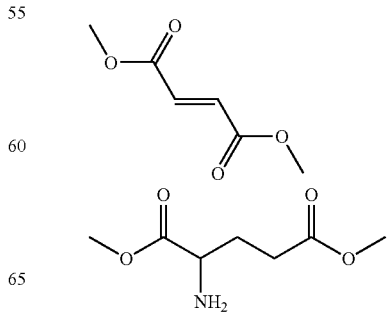

-continued
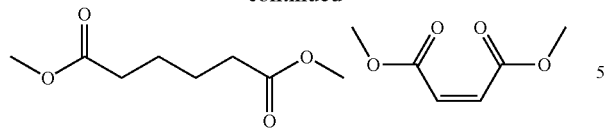
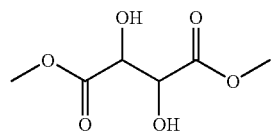
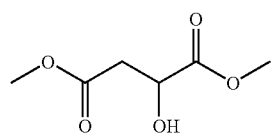
Preferably, the di-steroidal prodrug of estradiol is selected from the group consisting of
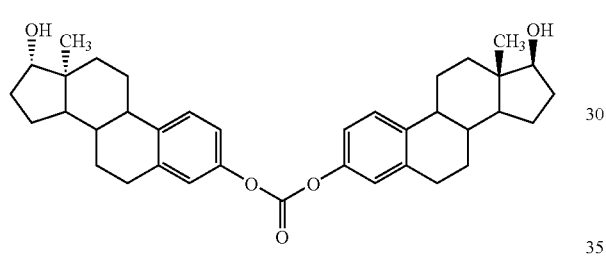
di-(3-estradiol)carbonate
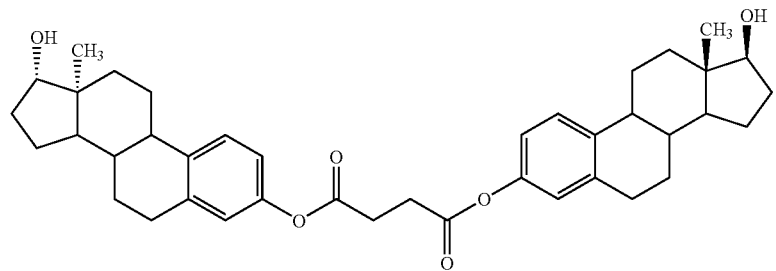
di-(3-estradiol)succinate
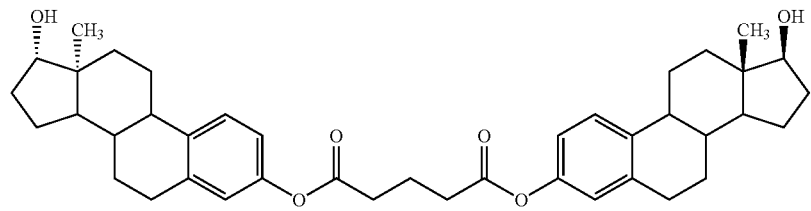
di-(3-estradiol)glutarate

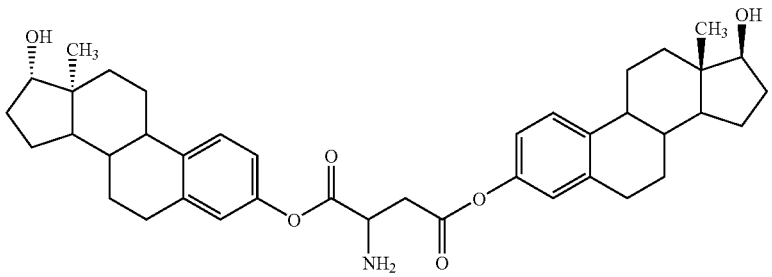

di-(3-estradiol)aspartate, and pharmaceutically acceptable salts thereof.

As used herein, the phrase "pharmaceutically acceptable salt" refers to a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, g-hydroxybutyrates, glycollates, tartrates, methane-sulfonates (mesylates), propanesulfonates, naphthalene-1-sulfonates, naphthalene-2-sulfonates, and mandelates. A desired salt may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, ftimaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid or ethanesulfonic acid, or the like. In the present invention the hydrochloride salt is the preferred salt.

A pharmaceutical dosage unit may be formulated to include the di-steroidal prodrug of ethinyl estradiol of the present invention in combination with one or more pharmaceutically acceptable excipients.

Excipients useful herein include a wide variety of additives, or ingredients, such as for example, fillers, diluents (solid and liquid), biocompatible polymers (such as organopolysiloxanes, polyurethanes and polymethylacrylates), skin penetrators and penetration enhancers, solubilizers, lubricants, stabilizers, flow control agents, colorants, glidants, effervescent agents, sweeteners, flavors, perfumes, and the like.

Other steroids, e.g., progestogens may be included in the pharmaceutical dosage unit. Exemplary progestogens include norethindrone, norethindrone acetate, norgestrel, levonorgestrel, desogestrel, 3-ketodesogestrel, gestodene, medroxyprogesterone acetate and the like.

The pharmaceutical dosage unit may be in an orally ingestible form, such as tablets, capsules, chewable tablets or capsules, troches, liquid suspensions, pills, or sustained release dosage forms. Alternatively, the pharmaceutical dosage unit may be a transdermal delivery system. Or in another embodiment the pharmaceutical dosage unit may be a topical composition such as a gel, cream, ointment, liquid and the like. Or in an alternative embodiment, the pharmaceutical dosage unit may be designed for vaginal administration e.g., a vaginal ring.

The steroidal prodrugs of estradiol may be synthesized using the methods described herein. These methods may be modified or alternative synthesis methods may be employed as desired. The synthesis methods typically begin with estradiol as the starting material. It should be understood, however, that where estradiol is indicated, derivatives of estradiol may be used.

In general, the di-steroidal prodrug of estradiol of the invention is formed by reacting estradiol or a derivative thereof and a suitable linking agent under conditions effective to form the di-steroidal prodrug of estradiol.

One method for synthesizing a di-steroidal ester of estradiol of this invention is by reacting estradiol or a derivative thereof with a carbonate linking agent and a coupling agent in the presence of a base. The resulting compound is di-(3-estradiol)carbonate. The reaction is depicted in Reaction Sequence 1.

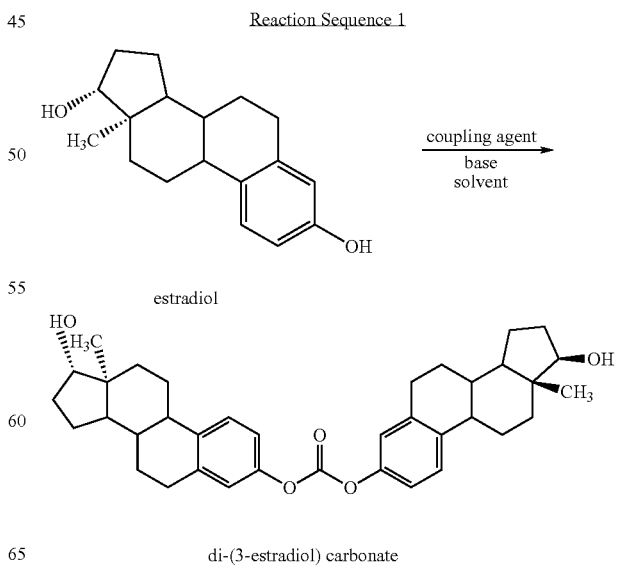

In a preferred embodiment, bis(4-nitrophenyl)carbonate (b-NPC) serves as the carbonate linking agent and coupling agent, 4-dimethylamino pyridine (DMAP) is selected as the base, and tetrahydrofuran (THF) is selected as the solvent.

Another method that may be used to synthesize a di-steroidal prodrug of estradiol of this invention reacts estradiol or a derivative thereof with an aliphatic diacid that has 1 to 10 carbon atoms, i.e., n is an integer from 1 to 10, which may be saturated or unsaturated and optionally may be substituted by one or more lower alkyl, hydroxy or amino groups. The aliphatic diacid is the linking agent and may be, for example, succinic acid, tartaric acid, malic acid, glutaric acid, adipic acid, fumaric acid, maleic acid, glutamic acid or aspartic acid. In one embodiment, a coupling agent can be reacted with a diacid in the presence of a base catalyst as shown in Reaction Sequence 2.

Reaction Sequence 2

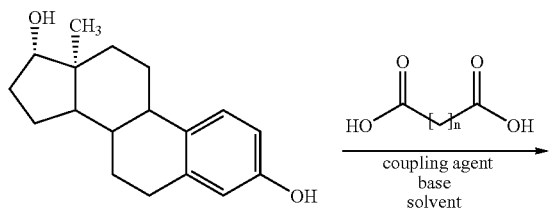

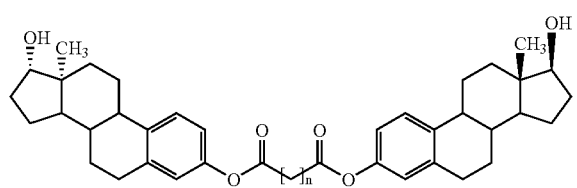

Reaction Scheme 2A shows a preferred embodiment where the coupling agent is 1-(3-dimethylaminopropyl)-3-ethyl-carbodiimide hydrochloride (EDCI) and the base catalysts are 4-dimethylamino pyridine (DMAP) and triethylamine. The solvent used to carry out the reaction is preferably chloroform, although as one skilled in the art will readily recognize, many other organic solvents may be suitable.

Reaction Scheme 2A

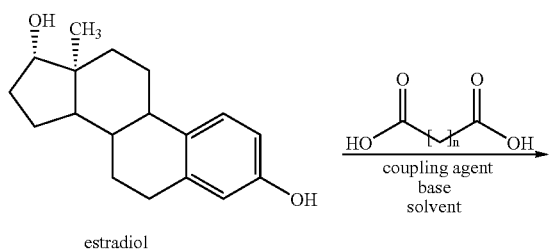

estradiol

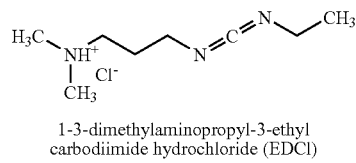

1-3-dimethylaminopropyl-3-ethyl carbodiimide hydrochloride (EDCl)

-continued

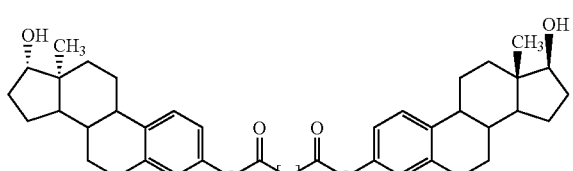

n = 2 di-(3-estradiol) succinate
n = 3 di-(3-estradiol) glutarate

The prodrug compound of this invention may also be synthesized by reacting estradiol or a derivative thereof directly with a linking agent having the formula

G-CO-Z-X-G wherein G is a halogen and Z and X are defined as previously noted. For example, the linking agent may be a di-acyl chloride which reacts with estradiol in the presence of a base, as depicted in Reaction Sequence 3.

Reaction Sequence 3

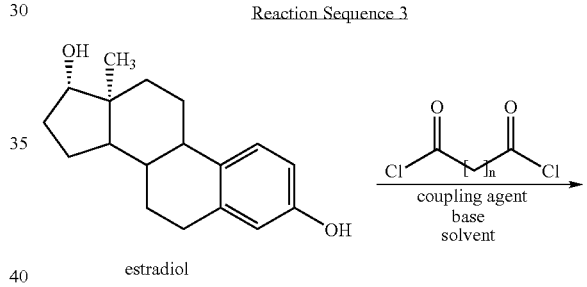

estradiol

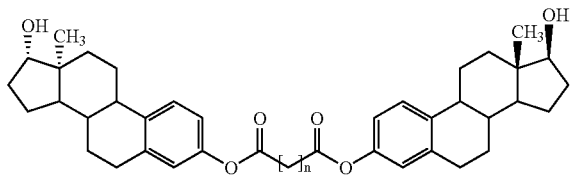

n = 2 di-(3-estradiol) succinate
n = 3 di-(3-estradiol) glutarate where n is an integer from 1 to 10

Utilizing Reaction Sequence 3, DMAP and triethylamine can be employed as the base catalysts.

Yet another method for forming the di-steroidal prodrug of estradiol of the invention is with a diacid amino acid, such as aspartic acid or glutamic acid, as the linking agent.

Reaction Sequence 4 exemplifies such a synthesis mechanism.

Reaction Sequence 4

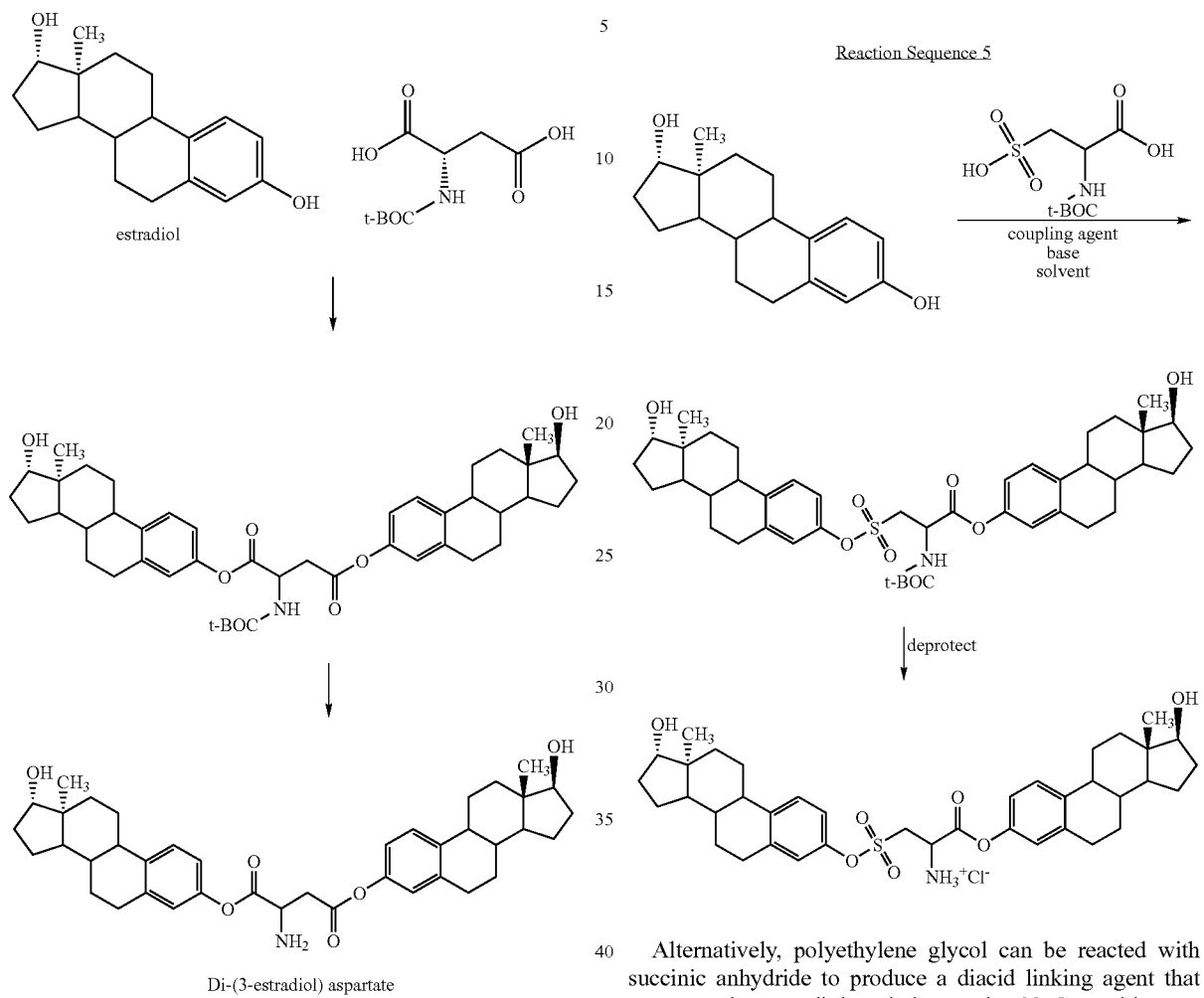

Di-steroidal prodrugs of estradiol may also be synthesized where tert-butoxycarbonyl cysteic acid serves as the linking agent, as depicted in Reaction Sequence 5.

Alternatively, polyethylene glycol can be reacted with succinic anhydride to produce a diacid linking agent that connects the estradiol moieties at the 3° C. position, as depicted in Reaction Sequence 6.

Reaction Sequence 6

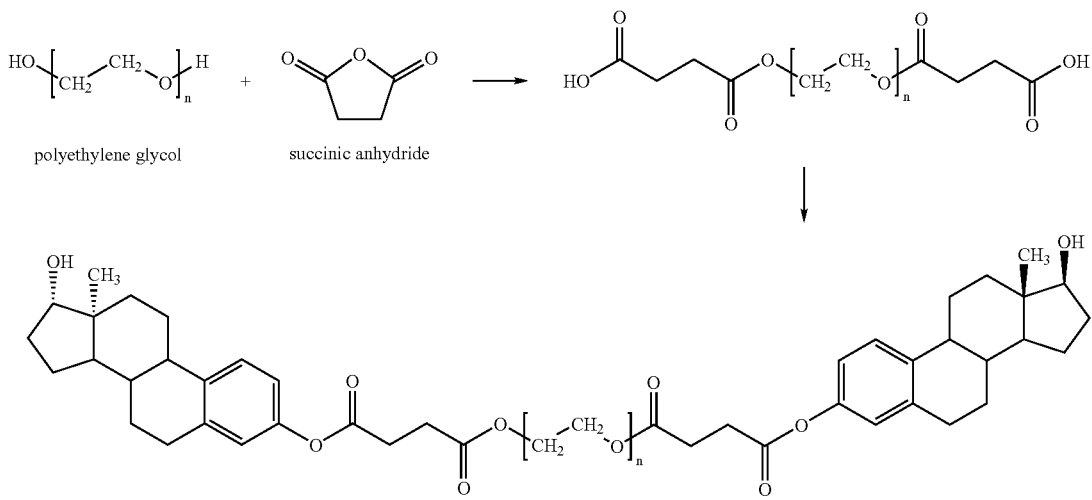

wherein n is an integer from 1 to 700, more preferably n is 4 to 200, and most preferably n is 4 to 60.

Moreover, estradiol may be reacted with a dipeptide or any suitable length of peptide, which serves as the linking agent. The peptide linking agent will have 2 to 15 units derived from amino acids, such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and combinations thereof. The end groups of the peptide are derived independently from aspartic acid or glutamic acid to form the divalent linking agent. From 2 to 15 amino acids may be linked together to form the peptide linker so long as the amino acids attached at the ends are aspartic acid, glutamic acid or a combination thereof. Preferably, 2 to 12 amino acids are linked together to form the peptide. More preferably, 2 to 5 amino acids form the divalent peptide. For example, the dipeptide Gly-Asp-Boc with the amine function protected with n-(tert butoxycarbonyl) can act as the linking group, as shown in Reaction Sequence 7.

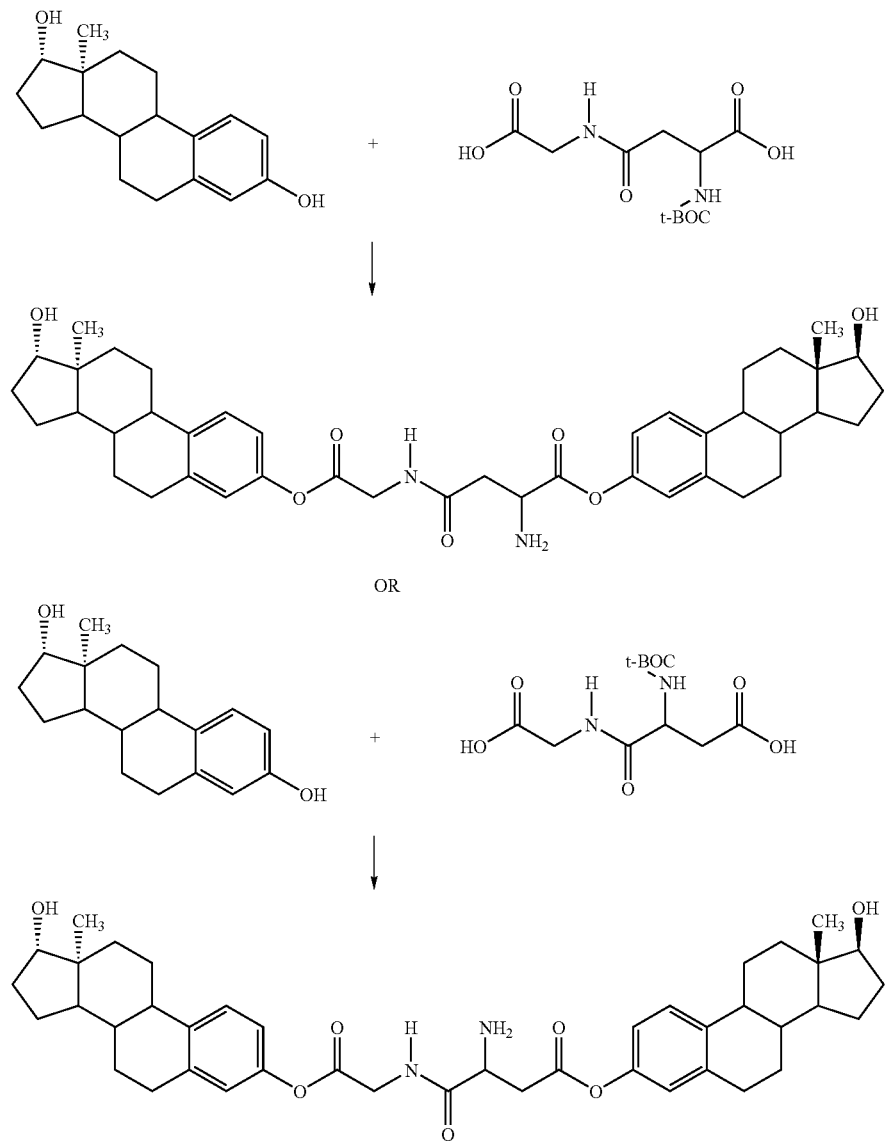

Preferably, the linking agents that are used to form the di-steroidal prodrug of estradiol of the invention are carbonate, H—Y-Z-X—H, or

G-CO-Z-X-G wherein G is a halogen. Z may be a divalent peptide group.

Coupling agents that may be used in synthesizing the di-steroidal prodrug of estradiol of the present invention, may be for example, b-NPC, EDCI, suitable alternatives or mixtures thereof. Alternative compounds may be used, so long as they fulfill the intended purpose.

In the synthesis reactions described, a base may be used as a catalyst. Suitable bases include, but are not limited to DMAP, triethylamine, or mixtures thereof.

Solvents that may be used in the synthesis reactions are for example, tetrahydrofuran (THF), chloroform, dichloromethane, and the like.

To increase the purity of the di-steroidal prodrug of estradiol, the prodrug may be treated to one or more washing steps, and/or recrystallization steps.

The washing step may be used to rinse the precipitate that is formed by the di-steroidal prodrug of estradiol. As noted, one or more washing steps may be used. Water, sodium hydroxide, or any suitable alternative can be generally used for washing purposes.

As previously noted, the purity may be increased by subjecting the di-steroidal prodrug to one or more recrystallization steps. The recrystallisation step may be performed by various methods, and using suitable solvents such as but not limited to ethyl acetate, heptane or THF, or mixtures thereof.

The drying step in the synthesis may be conducted by various methods including but not limited to, air drying, vacuum drying, oven drying, filtration, and the like. Drying may be enhanced by using a drying agent such as magnesium sulphate to assist in drying the product.

The di-steroidal prodrug of estradiol compounds of the present invention have been characterized using various analytical methods. For example, high performance liquid chromatography (HPLC) was used to establish the purity of the synthesized product. $^1H$ and $^{13}C$ nuclear magnetic resonance (NMR), mass spectrometry and infrared (IR) spectroscopy were used to verify its structure. Moreover, the product was further characterized by determining the melting point.

The di-steroidal prodrug of estradiol of the present invention may be used for providing contraception. A therapeutically effective amount of the di-steroidal prodrug of estradiol of the invention is administered to a patient in need thereof, for an effective period of time. Preferably, the di-steroidal prodrug is administered in combination with a progestogen.

The di-steroidal prodrug of estradiol of the invention can also be used in providing hormone treatment therapy. Such a method of treatment would comprised the step of administering to a patient in need thereof, a therapeutically effective amount of a di-steroidal prodrug of estradiol of the invention, for an effective period of time.

The prodrugs of estradiol of the present invention are administered in a "therapeutically effective amount." This is understood to mean a sufficient amount of a compound or composition that will positively modify the symptoms and/or condition to be treated. The therapeutically effective amount can be readily determined by those of ordinary skill in the art, but of course will depend upon several factors. For example, one should consider the condition and severity of the condition being treated, the age, body weight, general health, sex, diet, and physical condition of the patient being treated, the duration of the treatment, the nature of concurrent therapy, the particular active ingredient being employed, the particular pharmaceutically-acceptable excipients utilized, the time of administration, method of administration, rate of excretion, drug combination, and any other relevant factors. Typically, the amount of prodrug of estradiol of this invention administered on a daily basis will have a potency equivalent to about 0.025 to about 100 mcg of estradiol.

The prodrugs of the invention are preferably administered orally or vaginally. The preferred dosage forms are tablets or vaginal rings.

Specific embodiments of the invention will now be demonstrated by reference to the following examples. It should be understood that these examples are disclosed solely by way of illustrating the invention and should not be taken in any way to limit the scope of the present invention.

EXAMPLE 1

Synthesis of Di-(3-Estradiol)Carbonate

Preparation

Estradiol (37.5 g, 0.138 mol), b-NPC (21.0 g, 0.069 mol), DMAP (1.7 g, 0.0138 mol) and THF (400 mL) were added to a 1 L 3-neck round-bottom flask fitted with a magnetic stirrer. The reaction mixture was stirred at room temperature for 18 hours. 400 mL of dichloromethane (DCM) was added, and the reaction mixture was stirred for 10 minutes. The reaction mixture was poured into 1 L of water. 2M hydrochloric acid (50 mL) was added with stirring to extract the compound. The organic layer was separated and washed with dilute hydrochloric acid (20 ml of 2M hydrochloric acid in 1 L of water) and further washed with sodium hydroxide (4×1 L), then with water (2×1 L), separated, dried with magnesium sulphate, filtered and reduced to dryness. The resulting di-(3-estradiol)carbonate was slurried in hexane and filtered. This process was repeated, and the precipitates were combined and allowed to dry in air.

Recrystallization Method

Di-(3-estradiol)carbonate (13 g) and ethyl acetate (550 mL) were added into a 3-neck round-bottom flask fitted with a condenser and magnetic stirrer. The mixture was heated to reflux. The hot mixture was filtered. The filtrate was allowed to cool and recrystallized slowly. The di-(3-estradiol) carbonate was isolated by filtration and allowed to air dry.

The compound was analyzed by HPLC and found to be 99.3% pure. Structural analysis by $^{13}C$ and $^1H$ NMR and IR spectroscopy revealed that the 3'C to 3'C carbonate prodrug had formed. Mass Spectroscopy revealed formation of the compound. Melting point was found to be 192° C.

EXAMPLE 2

Synthesis of Di-(3-Estradiol)Succinate

Preparation

To a 3-neck round-bottom flask fitted with a magnetic stirrer was added estradiol (48.92 g; 0.18 mol), magnesium sulphate (400 g) and anhydrous THF (1 L). The mixture was stirred under nitrogen for 2 hours at room temperature, and then filtered. The filter cake was washed with anhydrous THF (100 ml). The filtrate was placed in a 3-neck round bottom flask and cooled to 0° C. under nitrogen. To this flask was added triethylamine (22.5 g, 0.22 mol) with stirring for 10 mins, followed by DMAP (1.66 g, 14 mmol) and the resulting solution stirred for 10 mins. A solution of succinyl chloride (14.59 g, 94 mmol) in anhydrous THF (250 ml) was added dropwise while keeping the temperature below 5° C. The reaction mixture was then stirred for 20 minutes at 0° C. and then overnight at room temperature. The reaction mixture was then filtered and the filter cake washed with THF (3×100 mL). The filtrate was concentrated in vacuo to leave an oily residue. The crude material was purified by dry column chromatography using ethyl acetate:hexane (60:40). Fractions containing the product spot were combined and concentrated to give a white powder.

The compound was analyzed by HPLC and found to be 92.8% pure. Structural analysis by $^{13}$C and $^1$H NMR and IR spectroscopy revealed that the 3'C to 3'C linked prodrug had formed. Melting point was found to be 210° C.

EXAMPLE 3

Synthesis of Di-(3-Estradiol)Glutarate

Preparation

To a 2 L 3-neck round-bottom flask fitted with a mechanical stirrer under nitrogen was added estradiol (50.0 g, 0.18 mol), magnesium sulfate (400 g) and anhydrous THF (1 L). The mixture was stirred for 2 hours at room temperature under nitrogen and filtered under nitrogen and the filter cake washed with anhydrous THF (100 mL). The filtrate was placed in a 2 L 3-necked round-bottomed flask and cooled to 0° C. (under nitrogen). To this was added triethylamine (23.30 g, 0.23 mol) with stirring for 10 minutes, DMAP (1.70 g, 13.9 mmol) and the resulting solution stirred for 10 min. A solution of glutaryl chloride (16.28 g, 96.3 mmol) in anhydrous THF (250 mL) was added dropwise while keeping the temperature below 5° C. The reaction mixture was then stirred for 1 hour at 0° C. and then overnight at room temperature. The reaction mixture was then filtered and the filter cake washed with THF (3×200 mL). The filtrate was concentrated in vacuo to leave an orange/brown solid. The crude material was purified by filtration through silica (1.5 kg) using ethyl acetate:hexane (50:50) as the elutant. Fractions containing the product spot were combined and concentrated.

The compound was analyzed by HPLC and found to be 92.0% pure. Structural analysis by $^{13}$C and $^1$H NMR and IR spectroscopy revealed that the 3' C to 3' C prodrug had formed. Melting point was found to be 204° C.

EXAMPLE 4

Synthesis of Di-(3-Estradiol)Aspartate

Preparation-Step 1

To a 1 litre 3-neck round-bottom flask fitted with a magnetic stirrer under nitrogen was charged N-(tert-butoxycarbonyl)aspartic acid (9.44 g; 0.04 mol), and chloroform (440 ml) with stirring. EDCI (27.60 g, 0.14 mol), and triethylamine (17.88 ml) were added and stirred for 15 minutes. Estradiol (20.00 g; 0.07 mol) was charged followed by DMAP (2.24 g, 0.018 mol). The solution was stirred for 20 hours at room temperature under an atmosphere of nitrogen. The reaction mixture was diluted with chloroform (400 ml), and washed successively with a 2M hydrochloric acid solution (2×400 ml) then brine (400 ml) and finally saturated sodium bicarbonate solution (2×400 ml). The organic layer was dried over magnesium sulphate filtered and concentrated to afford a white solid. The crude material was purified by dry column on silica using a gradient elution of Hexane:Ethyl acetate 70:30 to 60:40. Fractions containing product were combined and concentrated to afford a white solid.

Preparation-Step 2. Deprotection Reaction

To a 250 ml 3-neck round-bottom flask fitted with a magnetic stirrer under nitrogen was charged the di-(3-estradiol) aspartate (Boc protected) (16 g; 0.02 mol) and 4M hydrochloric acid in dioxane (80 ml). The solution was stirred at room temperature under nitrogen for 18 hours. The reaction mixture was concentrated in vacuo, and the residue dissolved in dichloromethane and then evaporated to dryness. This residue was then slurried in diethyl ether and the resulting white precipitate filtered. The solid was then slurried in hot acetone, filtered, washed with hexane and dried to afford a white solid.

The compound was analyzed by HPLC and found to be 77.7% pure. Structural analysis by $^{13}$C and $^1$H NMR and IR spectroscopy revealed that the 3' C to 3' C prodrug had formed.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A di-steroidal prodrug of estradiol having the following formula:

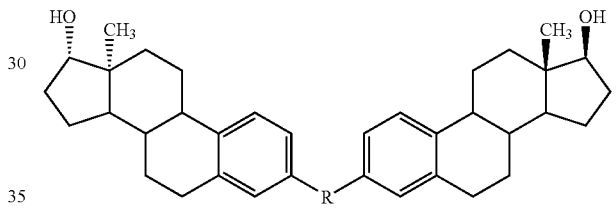

wherein R is selected from the group consisting of

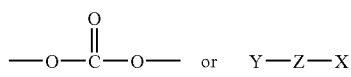

wherein X and Y are independently selected from

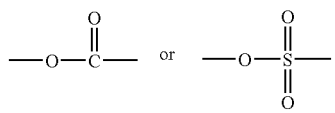

and Z is (i) an aliphatic straight chain having 1 to 10 carbon atoms which may be saturated or unsaturated and optionally may be substituted by one or more lower alkyl, hydroxy or amino groups, (ii) A-B-D wherein A and D are independently

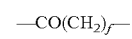

wherein f is 0 to 5, and B is —O—$(CH_2CH_2O)_p$—, wherein p is 1 to 700, or (iii) a peptide linkage having 2 to 15 amino acid units derived independently from amino acids selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or combinations thereof wherein the end groups of the peptide are amino acid units independently derived from aspartic acid and glutamic acid.

2. The prodrug of claim 1, wherein R is

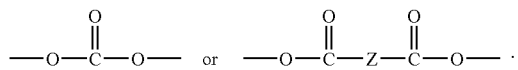

3. The prodrug of claim 1, wherein R is selected from the group consisting of:

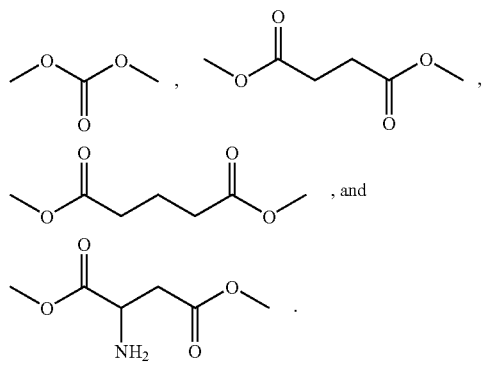

4. The prodrug of claim 1, wherein R is:

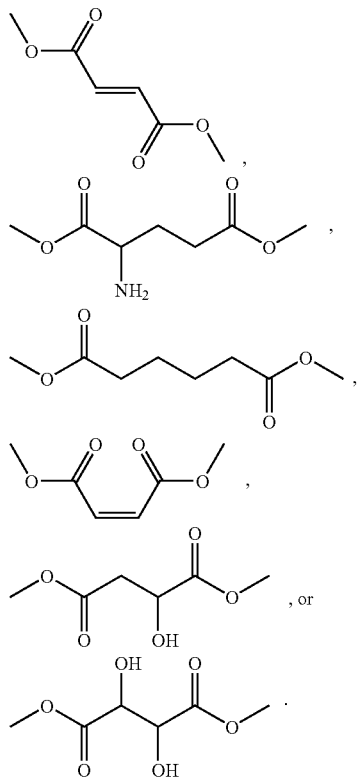

5. The prodrug of claim 1, wherein said prodrug is selected from the group consisting of di-(3-estradiol)carbonate, di-(3-estradiol)succinate, di-(3-estradiol) glutarate and di-(3-estradiol)aspartate.

6. A pharmaceutical composition comprising:
   (a) a di-steroidal prodrug of estradiol having the following formula:

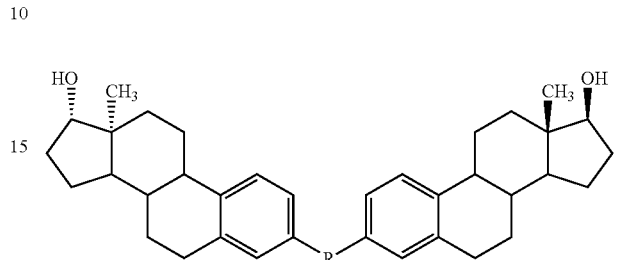

wherein R is selected from the group consisting of

wherein X and Y are independently selected from

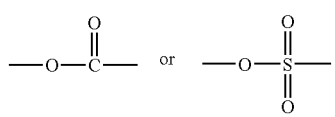

and Z is
   (i) an aliphatic straight chain having 1 to 10 carbon atoms which may be saturated or unsaturated and optionally may be substituted by one or more lower alkyl, hydroxy or amino groups,
   (ii) A-B-D
wherein A and D are independently

wherein f is 0 to 5, and B is $O-(CH_2CH_2O)_p-$, wherein p is 1 to 700, or
   (iii) a peptide linkage having 2 to 15 amino acid units derived independently from amino acids selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or combinations thereof wherein the end groups of the peptide are amino acid units independently derived from aspartic acid and glutamic acid, and
   (b) one or more pharmaceutically acceptable excipients.

7. A method of synthesizing a di-steroidal prodrug of estradiol having the formula

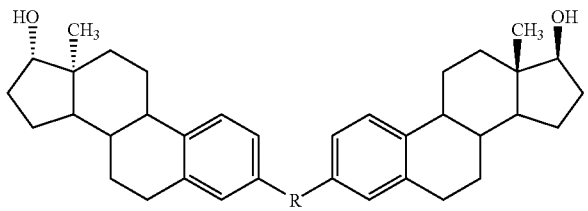

wherein R is selected from the group consisting of

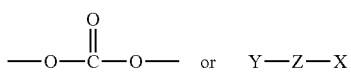

wherein X and Y are independently selected from

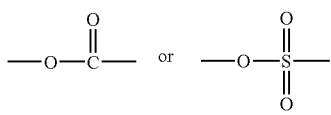

and Z is
- (i) an aliphatic straight chain having 1 to 10 carbon atoms which may be saturated or unsaturated and optionally may be substituted by one or more lower alkyl, hydroxy or amino groups,
- (ii) A-B-D wherein A and D are independently
—CO(CH$_2$)$_f$— wherein f is 0 to 5, and B is —O—(CH$_2$CH$_2$O)$_p$—, wherein p is 1 to 700, or
- (iii) a peptide linkage having 2 to 15 amino acid units derived independently from amino acids selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or combinations thereof wherein the end groups of the peptide are amino acid units independently derived from aspartic acid and glutamic acid, comprising the steps of:
- (A) providing estradiol or a derivative thereof;
- (B) admixing said estradiol and a linking agent, wherein said linking agent is selected from the group consisting of:
  - (a) a carbonate;
  - (b) an aliphatic diacid having a backbone of 1 to 10 carbon atoms;
  - (c) G-CO-Z-X-G
    wherein G is a halogen;
  - (d) a peptide linkage having 2 to 15 amino acid units derived independently from amino acids selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or combinations thereof wherein the end groups of the peptide are amino acid units independently derived from aspartic acid and glutamic acid;
  - (e) a tert-butoxycarbonyl protected cysteic acid; and
  - (f) a polyethylene glycol and succinic anhydride,
- (C) optionally, admixing a coupling agent and/or a base, thereby forming said di-steroidal prodrug of estradiol or pharmaceutically acceptable salt thereof.

8. The method of claim 7, wherein said linking agent is a carbonate,

H—Y-Z-X—H, or

G-CO-Z-X-G wherein G is a halogen.

9. The method of claim 7, wherein said coupling agent is selected from the group consisting of: bis(4-nitrophenyl) carbonate, 1-(3-dimethylaminopropyl)-3-ethyl-carbodiimide hydrochloride, and mixtures thereof.

10. The method of claim 7, wherein said at least one base is selected from the group consisting of: 4-dimethylamino pyridine, triethylamine, and mixtures thereof.

11. The method of claim 7, wherein said prodrug is di-(3-estradiol)carbonate or a pharmaceutically acceptable salt thereof.

12. The method of claim 7, wherein said prodrug is selected from the group consisting of: di-(3-estradiol) succinate, di-(3-estradiol)glutarate, di-(3-estradiol)aspartate, and a pharmaceutically acceptable salts thereof.

13. A method of providing contraception comprising the step of:
administering to a patient in need thereof, an effective amount of said di-steroidal prodrug of estradiol of claim 1, for an effective period of time.

14. A method of providing hormone treatment therapy to a patient in need thereof, comprising the step of:
administering to said patient in need thereof, an effective amount of said di-steroidal prodrug of estradiol of claim 1, for an effective period of time.

* * * * *